(12) United States Patent
Adamo et al.

(10) Patent No.: US 9,041,925 B2
(45) Date of Patent: May 26, 2015

(54) LASER DIFFRACTION WITH INHALER ENCLOSED IN POSITIVE PRESSURE CHAMBER

(71) Applicant: MannKind Corporation, Valencia, CA (US)

(72) Inventors: Benoit Adamo, Mount Kisco, NY (US); Saiyam Shah, Valencia, CA (US); Chad C. Smutney, Watertown, CT (US)

(73) Assignee: MannKind Corporation, Valencia, CA (US)

( * ) Notice: Subject to any disclaimer, the term of this patent is extended or adjusted under 35 U.S.C. 154(b) by 94 days.

(21) Appl. No.: 13/939,060

(22) Filed: Jul. 10, 2013

(65) Prior Publication Data

US 2013/0308130 A1    Nov. 21, 2013

Related U.S. Application Data

(62) Division of application No. 12/727,179, filed on Mar. 18, 2010, now Pat. No. 8,508,732.

(60) Provisional application No. 61/161,379, filed on Mar. 18, 2009.

(51) Int. Cl.
| | |
|---|---|
| A61M 99/00 | (2012.01) |
| G01N 15/06 | (2006.01) |
| A61M 15/00 | (2006.01) |
| A61M 11/00 | (2006.01) |
| G01N 15/02 | (2006.01) |

(52) U.S. Cl.
CPC ............... *G01N 15/06* (2013.01); *A61M 15/00* (2013.01); *A61M 2202/064* (2013.01); *A61M 2209/02* (2013.01); *G01N 15/0205* (2013.01); *G01N 15/0211* (2013.01); *A61M 11/001* (2014.02)

(58) Field of Classification Search
CPC .......... G01N 15/0211; G01N 15/0205; A61M 2202/064; A61M 2209/02; A61M 11/001
See application file for complete search history.

(56) References Cited

U.S. PATENT DOCUMENTS

| | | | |
|---|---|---|---|
| 4,811,731 | A  | 3/1989 | Newell et al. |
| 6,279,511 | B1 | 8/2001 | Loughnane |
| 7,305,986 | B1 | 12/2007 | Steiner et al. |
| 7,414,720 | B2 | 8/2008 | Wachtel et al. |
| 7,453,556 | B2 | 11/2008 | Hochrainer et al. |

(Continued)

FOREIGN PATENT DOCUMENTS

| | | |
|---|---|---|
| JP | 2001-133384 | 5/2001 |
| JP | 2007-061281 | 3/2007 |

(Continued)

OTHER PUBLICATIONS

Boer et al., Design and application of a new modular adapter for laser diffraction characterization of inhalation aerosols. International Journal of Pharmaceutics 249: 233-245 (2002).

(Continued)

*Primary Examiner* — Hwa Lee
(74) *Attorney, Agent, or Firm* — K&L Gates LLP; Louis C. Cullman; Robert W. Winn

(57) ABSTRACT

The present disclosure relates to an improved device and methods for adapting to a laser diffraction apparatus used for measuring particle size distribution and density of the plume of a powder composition emitted from a dry powder inhaler.

19 Claims, 12 Drawing Sheets

(56) References Cited

U.S. PATENT DOCUMENTS

| | | |
|---|---|---|
| 7,464,706 B2 | 12/2008 | Steiner et al. |
| 8,172,817 B2 | 5/2012 | Michaels et al. |
| 8,508,732 B2 | 8/2013 | Adamo |
| 2002/0101590 A1 | 8/2002 | Shimaoka |
| 2002/0144680 A1 | 10/2002 | Nilsson et al. |
| 2003/0054566 A1* | 3/2003 | Hochrainer et al. .......... 436/181 |
| 2004/0163648 A1 | 8/2004 | Burton |
| 2007/0006876 A1 | 1/2007 | Finlay et al. |
| 2008/0015457 A1 | 1/2008 | Silva |
| 2008/0255468 A1 | 10/2008 | Derchak et al. |
| 2009/0149727 A1 | 6/2009 | Truitt et al. |
| 2009/0151720 A1 | 6/2009 | Inoue et al. |
| 2009/0308391 A1 | 12/2009 | Smutney et al. |
| 2010/0235116 A1 | 9/2010 | Adamo et al. |
| 2011/0000482 A1 | 1/2011 | Gumaste et al. |

FOREIGN PATENT DOCUMENTS

| | | |
|---|---|---|
| WO | 2002/059574 A1 | 8/2002 |
| WO | 2005/081977 A2 | 9/2005 |
| WO | 2008/060484 A2 | 5/2008 |
| WO | 2010/108046 A1 | 9/2010 |

OTHER PUBLICATIONS

International Search Report mailed on Jul. 1, 2010 for International Application No. PCT/US2010/027880 filed on Mar. 18, 2010.
Sympatecs Dry Dispersion Units, Dry Dispersion for Laser Diffraction and Image Analysis. ZP-002586530.
International Search Report mailed on Nov. 19, 2014 for International Application No. PCT/US2014/049817 filed on Aug. 5, 2014.
Skyler, Pulmonary insulin: current status. Diabetes Voice, vol. 51, Issue I, p. 23-25, 2006.
Wright et al., Inhaled Insulin: Breathing new life into diabetes therapy. Nursing, vol. 37, No. 1, p. 46-48 (2007).

* cited by examiner

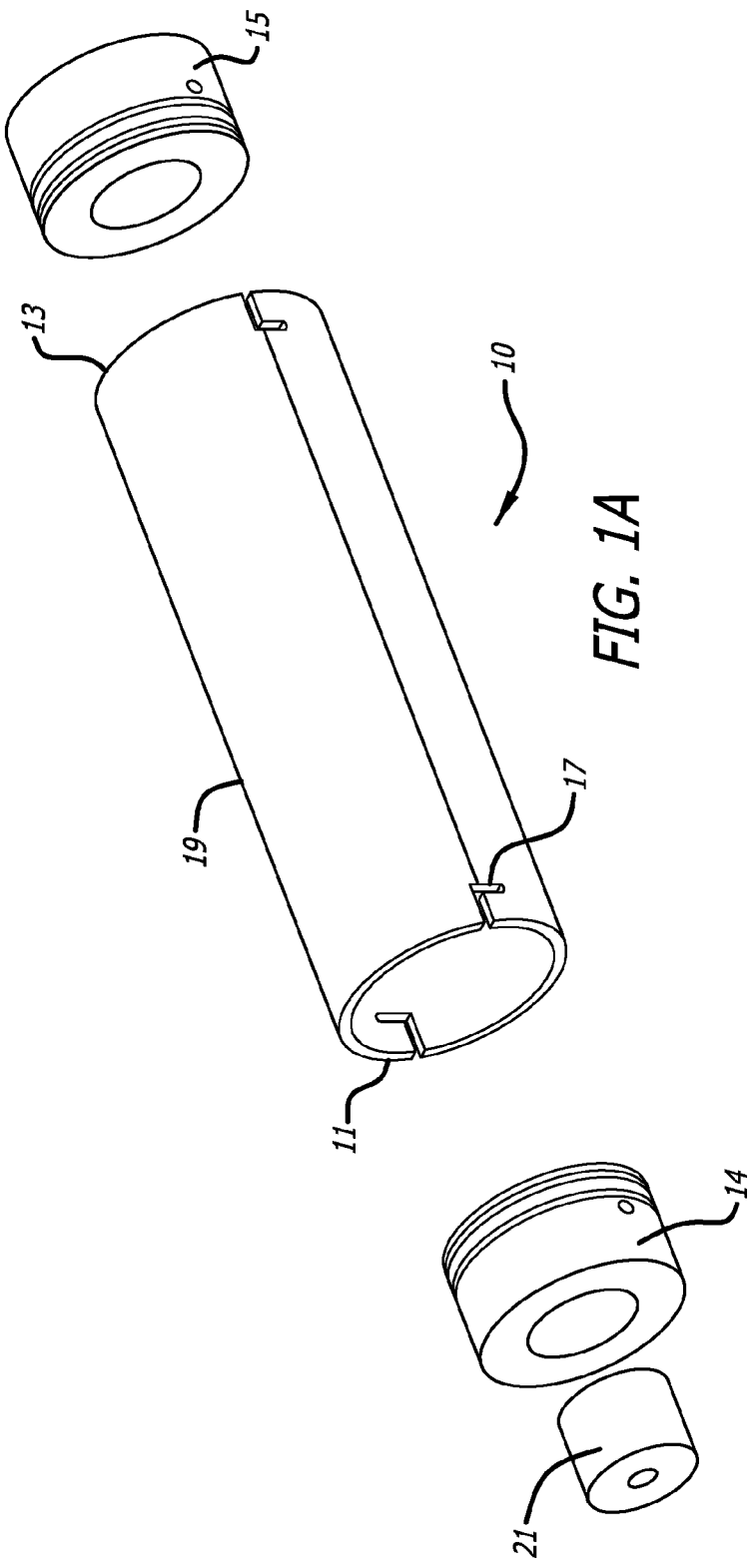

LASER DIFFRACTION WITH INHALER ENCLOSED IN POSITIVE PRESSURE CHAMBER

CROSS REFERENCE TO RELATED APPLICATIONS

This application is a divisional patent application of U.S. patent application Ser. No. 12/727,179 filed Mar. 18, 2010, which claims the benefit under 35 U.S.C. §119(e) from U.S. Provisional Patent Application Ser. No. 61/161,379, filed on Mar. 18, 2009, the contents of which are incorporated herein by reference in their entirety.

TECHNICAL FIELD

The present disclosure relates to an improved device and method for use with a laser diffraction apparatus. In particular, the device is used as an adaptor for dry powder inhalers and provides a more consistent method for more accurately measuring particle size distribution and density of a plume of a powder composition emitted from a dry powder inhaler.

All references cited in this specification, and their references, are incorporated by reference herein in their entirety where appropriate for teachings of additional or alternative details, features, and/or technical background.

BACKGROUND

Dry powder inhalers such as those described in U.S. Pat. Nos. 7,305,986, 7,464,706 and U.S. patent application Ser. No. 12/484,129 (2009/0308391), which disclosure is incorporated herein by reference in their entirety, can generate primary drug particles or suitable inhalation plumes during an inspiratory maneuver by deagglomerating the powder formulation within a capsule or a cartridge. Dosing reproducibility requires that the drug formulation is uniform and that the dose can be delivered to the patient with consistent and reproducible results. Therefore, the dosing system must operate to completely discharge all of the formulation effectively during an inspiratory maneuver when the patient is taking his/her dose. The benefits of delivering drugs via the pulmonary circulation are numerous and include, rapid absorption into the arterial circulation, avoidance of drug degradation by liver metabolism, ease of use, i.e., lack of discomfort of administration, such as discomfort encountered by other routes of administration, for example, by subcutaneous and intravenous injections.

The consistency in drug delivery from an inhaler is due in part to the consistency in resistance to air flow within the air passages of the inhalation device. High resistance dry powder inhalers such as those disclosed in U.S. Pat. Nos. 7,305,986 and 7,464,706, and U.S. patent application Ser. No. 12/484,129 (2009/0308391), deliver drug formulations in a consistent manner. One of the parameters used to ascertain or predict if an inhaler would deliver a dose with consistency during use is the resistance to air flow of the device, which is due in part to the internal geometries of the air conduits. Another parameter related to dosing consistency is the quality of the powder plume generated from the inhaler during use, which is dependent on various factors, for example, the type of dry powder and the inhaler system's ability to deagglomerate the powder into fine particles that can reach the lungs during an inhalation.

Present systems and methods for measuring particle distribution are commercially available, however, the commercial apparatuses are targeted to be used for relatively lower resistance inhalers. For example, in one standard method, an inhaler module uses laser diffraction technology to quantify particle size distribution in dry powder inhalers (DPI). The standard inhaler module is comprised of a chamber in which the inhaler is mounted outside in ambient air and the plume travels through an enclosed chamber. The plume is formed by a vacuum generated across the chamber and powder flows through the device. Midway through the chamber, the powder plume travels through the zone in which the laser is projected thus causing the laser beam to diffract after colliding with the particles. A collection of sensors across from the laser source measure these diffraction patterns and, using Mie theory (an analytical solution of equations for the scattering of electromagnetic radiation by spherical particles), interpret them to quantify particle size distribution of the inhaler powder discharge in the plume. In use, the vacuum can generate areas of high and low pressure within the chamber, creating a non-uniform plume.

In this standard set up, the way in which the plume moves through the chamber will affect the system's ability to accurately quantify the particle size distribution of the powder plume. For instance, the plume residence time in the chamber is critical to accurate measurement. Ideally, the system should be able to measure the plume in real time. For example, if the plume is discharged over a time interval of 0.5 seconds, the standard system should be able to detect and measure the plume in approximately 0.5 seconds.

There are several other parameters that can affect the measurement of the particle size distribution of a plume in a chamber. For example, variations in environmental effects inside the chamber, such as turbulence, certain sized powder particles will spend increased amount of time in the measurement zone. This behavior would cause the particles to be measured multiple times (at least more than once), thus increasing their relative presence within the overall particle size distribution which leads to erroneous representation of actual data.

Additionally, particle size distribution measurements made using prior art systems and relatively small inhalation devices are inconvenient to use and yield erroneous or irreproducible results due to the variations in conditions provided by the chamber, for example, powder deposition in internal surfaces, including the lenses of the adaptor which can result in additional diffractions. Additionally, the adaptor and lenses must be cleaned repeatedly after each use, due to the increased turbulence generated inside the device as described above, all of which can lead to inconsistent measurements of the powder plume.

Therefore, the inventors have seen the need to design and manufacture a simple device for adapting to any laser diffraction apparatus, and a method for measuring particle distribution to ascertain the powder characteristics emitted by an inhaler in use for determining the quality of the powder and effectiveness of the inhaler in dosing a patient.

SUMMARY

Disclosed herein is a device configured to be adapted to a laser diffraction apparatus and/or system and for use with inhalation devices. A method for measuring particle size distribution of a powder plume emitted by an inhalation system and/or device during testing with a powder formulation is also disclosed.

In embodiments described herein, the device comprises an adaptor configured in any shape or size depending on the inhaler to be used or to be tested. In one embodiment, the adaptor or device comprises a tubular or cylindrical structure having a chamber and opposing ends, including a proximal end and a distal end; the distal end being configured to be closed and having an opening to connect a tubing to allow pressurized air or gas into the chamber; the proximal end comprising an inhaler mounting means which closes the end and is configured to adapt to a cap over the proximal end of the chamber having a structure to form a tight seal so that when an inhaler is mounted, an air conduit forms only though the inhaler and the inhaler is enclosed within the chamber. In one embodiment, the proximal end cap can comprise a mouthpiece adaptor, a mouthpiece adaptor case, a gasket, a mouthpiece adaptor cover, an end cap and a clamp configured to be attachable and to be mounted onto a mounting plate which is connected to a base plate.

In certain embodiments and depending on the inhaler design, the chamber may comprise a closed structure with an inlet port configured to receive a source of positive pressure and an outlet port configured to hold the mouthpiece portion of an inhaler, and wherein end caps can be optionally provided.

In another embodiment, the adaptor or device can comprise a securing means including a clamp configured to be mounted onto a platform and configured to hold or immobilize the chamber. In one embodiment, immobilization of the chamber can be at one end of the chamber, for example, at the proximal end. In one embodiment, the device comprises a chamber having a void, wherein the chamber comprises a spacer and an end cap. In one embodiment, the spacer is configured to be insertable into the chamber so as to minimize or reduce the size of the void in maintaining the chamber size constant for different inhaler types to be tested.

In one embodiment, the device is configured to be adapted to a laser diffraction apparatus, and comprises a cylinder configured to enclose a breath-powered, dry powder inhaler and having a distal end and proximal end, a first end cap configured to adapt to said distal end and a second end cap configured to adapt to said proximal end; said first end cap configured having an opening for adapting a tubing connected to a flow meter; said proximal end configured to have a holder configured to mount said breath-powered, dry powder inhaler. In one embodiment, the device comprises gaskets and/or o-rings for making a tight seal with the first end cap and the second end cap and the second end cap is configured to have an inhaler mouthpiece adaptor.

In one embodiment, a method of measuring particle distribution with a laser diffraction apparatus, comprises providing a device configured to hold a breath-powered, dry powder inhaler in a closed environment; installing an inhaler comprising a dry powder medicament onto the device and providing positive pressure driven flow, including air or gas into the device to pressurize and create a plume of powder exiting the inhaler, and measuring with the laser diffraction apparatus the particles emitted from the inhaler in a chamberless and/or ambient environment. In one embodiment, the plume of discharged powder is vacuumed into a disposable system after it is measured; wherein the vacuum source is provided at about 200 to about 250 millibars or at a flow rate greater than 30 L/min.

In another embodiment, a method of measuring particle size distribution with a laser diffraction apparatus, comprising: providing a device configured to hold a breath-powered, dry powder inhaler in a closed environment; said breath-powered inhaler comprising a dry powder formulation; installing said breath-powered inhaler into said device; actuating a laser diffraction system adapted with said device; providing a flow of compressed air or gas into the device to pressurize the device and create a flow of air or gas through the inhaler so that the dry powder formulation is discharged into a plume of powder exiting the inhaler, and measuring with the laser diffraction apparatus the particles emitted from the inhaler in a chamberless and/or environment in ambient conditions and under a vacuum. In one embodiment, the vacuum source is provided at about 250 millibars; or at a flow rate greater than 30 L/min. In this an other embodiments, peak flow rates generated by the positive pressure provided to generate the powder plume discharge from an inhaler range from about 10 to about 40 L/min.

In one embodiment, a device is configured to adapt to a laser diffraction apparatus is disclosed, the device comprising: a chamber configured to enclose a breath-powered, dry powder inhaler; said chamber having a distal end and proximal end, and a first end cap configured to adapt to said distal end and a second end cap configured to adapt to said proximal end; said first end cap having an opening configured to receive a tubing which is connected to a flow valve controller; said proximal end configured to have a mouthpiece mounting means configured to hold said breath-powered, dry powder inhaler.

In yet another embodiment, a device configured to adapt to a laser diffraction apparatus is disclosed, comprising: a chamber configured to enclose a breath-powered, dry powder inhaler having a mouthpiece and a body, and wherein said chamber has a distal end and proximal end, a void, an inlet port and an outlet port; one or more end caps configured to adapt to said inlet port and/or said outlet port, said inlet port configured to receive a source of positive pressure, and an inhaler mounting means having an opening and configured to hold an inhaler mouthpiece in place in said opening; and an device mounting means; wherein a breath powered, dry powder inhaler installed in said inhaler mounting means has its body enclosed within said chamber and forms an air pathway between the chamber void and a chamberless and/or ambient environment.

In another embodiment, a method of measuring particle size distribution with a laser diffraction apparatus is provided, comprising: providing a device comprising a chamber and configured to hold a breath-powered, dry powder inhaler in a closed environment; the breath-powered inhaler having a body and comprising a dry powder formulation; installing the breath-powered inhaler into the chamber so that the body of said dry powder inhaler is enclosed within the chamber; providing positive pressure into the chamber of the device to create a flow of air or gas through the dry powder inhaler to discharge particles of the dry powder formulation, and measuring with the laser diffraction apparatus the particles emitted from the inhaler into a chamberless and/or ambient environment. In one embodiment, the method can be applied to breath-powered, dry powder inhalers comprises a mouthpiece and a body, wherein the mouthpiece forms an air pathway from the chamber to the chamberless and/or ambient environment. In one embodiment, the step of providing positive pressure into the chamber is attained by a source of pressurized gas from a flow controller system comprising a valve or a syringe pump and the positive pressure applied is greater than 1 kPa. In another embodiment, the method comprises the step of measuring with a laser diffraction apparatus the emitted powder particle discharge which occurs concurrent with emission of particles from the inhaler.

In embodiments described herewith, the device and method can enable performance evaluations of an inhaler from analyses of the particle size distribution and density of the powder discharged with consistency and reproducibility, using any source of positive pressure, including pressurized air or gas such as nitrogen, and at controlled temperature, pressure, humidity and flow rates. In one embodiment, the positive pressure used to deliver a discharge from an inhaler in a chamber generates peak flow rates greater than 5 L/min, or greater than 10 L/min. In a particular embodiment, the peak flow rates range from about 10 to about 50 L/min. In another embodiment, the distance from the inhaler mouthpiece opening to the vacuum source hose opening can be greater than 5 cm. In one particular embodiment, the distance from the inhaler mouthpiece opening to the vacuum source hose opening greater than 5 cm.

BRIEF DESCRIPTION OF THE DRAWINGS

FIG. 1A depicts a perspective view of an embodiment of the device for adapting to a laser diffraction particle measuring apparatus in a partially exploded configuration.

DETAILED DESCRIPTION

In embodiments disclosed herein, there is disclosed a device and method for use with a laser diffraction apparatus and system for measuring size distribution and density of particles from a plume of powder discharged from an inhaler. In the embodiments described herein, the device provides an advantageous method for measuring the particle size distribution of a powder plume emitted from a breath-powered inhaler because the plume can cross through the measuring space without obstruction or disturbance from chamber induced factors.

In an embodiment exemplified herewith, the device can be made from any material including metals, composites and/or plastics, and enables the use of positive pressure-driven instead of vacuum-driven system, which are conventionally used, for example, with the Helios System by Sympatec GmbH. In this embodiment, positive pressure provided to a chamber containing an inhaler with a powder dose is used to drive a powder contained in an inhaler to flow through the inhaler and discharge through the inhaler mouthpiece in a substantial horizontal axis across ambient air traversed by a substantially perpendicular laser beam. In this and other embodiments, a test inhaler comprising a powder is placed within a chamber and the chamber is closed; the system is activated and the flow controlling valve allows air to flow into the chamber at a predetermined rate depending on the inhaler type.

Figure 1B:
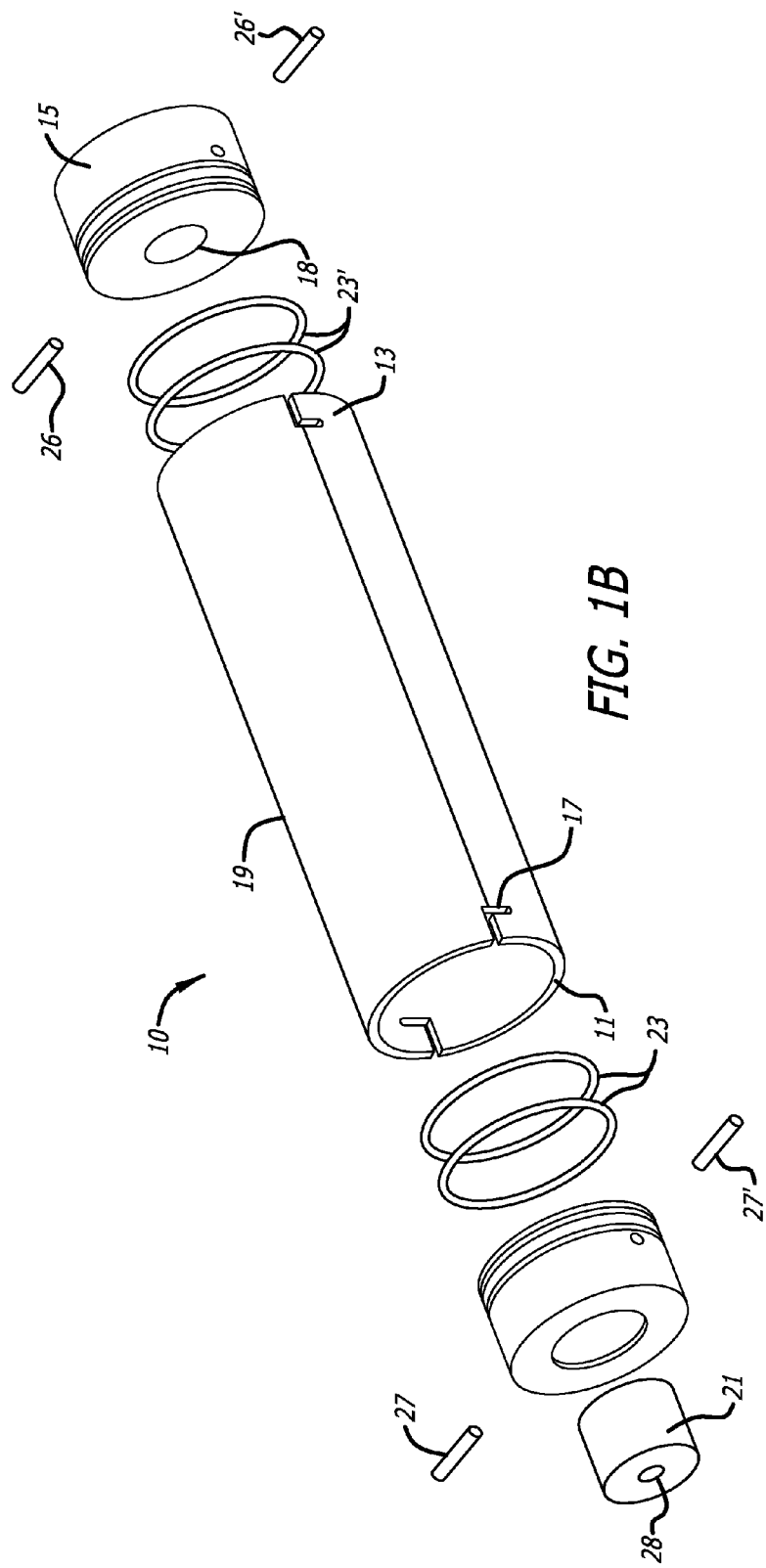
FIG. 1B is an exploded view of FIG. 1A, showing all components parts.

In an embodiment illustrated in FIGS. 1A and 1B, the adaptor or device 10 can comprise a structure with two or more openings, at least two are at opposing ends, proximal 11 and distal end 13 and at least one end, distal end 13 is configured to communicate with a source of pressurized air or a gas, for example, nitrogen; and the opposing end 11 is proximal to the area of a laser beam 32 (FIG. 3) emitting device 20 for measuring the particle size distribution of a powder plume emitted from an inhaler, for example, inhaler 30.

Figure 5:
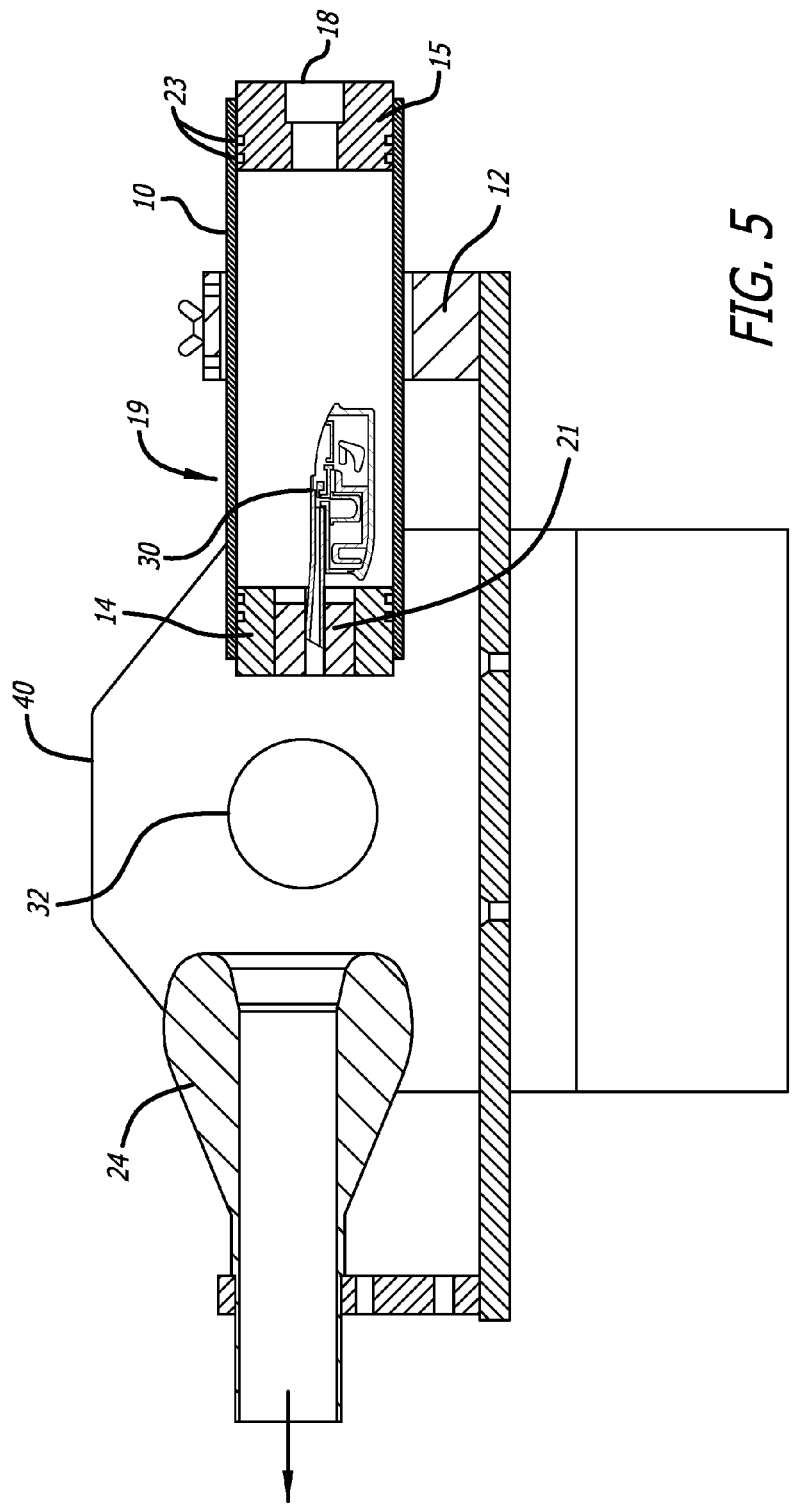
FIG. 5 depicts a schematic illustration of an embodiment of the device in cross-section through its mid-longitudinal axis showing an inhaler adapted to the holder in an in-use position.

FIG. 1B is an exploded view of the embodiment illustrated of FIG. 1A, further showing device 10 also comprises slots 17, for securing a lid or end caps 14, 15 placed at opposing ends 11, 13 to close the cylinder or chamber 19. Device 10 further comprises a holder or an inhaler adapter 21 as mounting means and comprising an opening 28 configured to receive a mouthpiece end of an inhaler 30 (FIG. 5). FIG. 5 depicts a schematic representation of an inhaler 30 mounted on device 10, located at one end of cylinder 19, installed into an inhaler adaptor 21 configured to seal the proximal end of the device 10. End cap 15 is configured to adapt to distal end 13 in such a way that it is flush with the outside surface of the end cap 14. The back end 13 of chamber 19 is connected to a low resistance flow meter and pressure line (not shown) through opening 18. The system uses flow control valves to create predetermined inspiratory flow profiles that move through an inhaler to disperse a powder. Device 10 also comprises O-rings 23, 23' adapted to the end caps 14, 15 for making a tight seal; pins 26, 26', 27, 27' are configured to adapt to the end caps for securing end caps 14, 15 to chamber 19.

Figure 2:
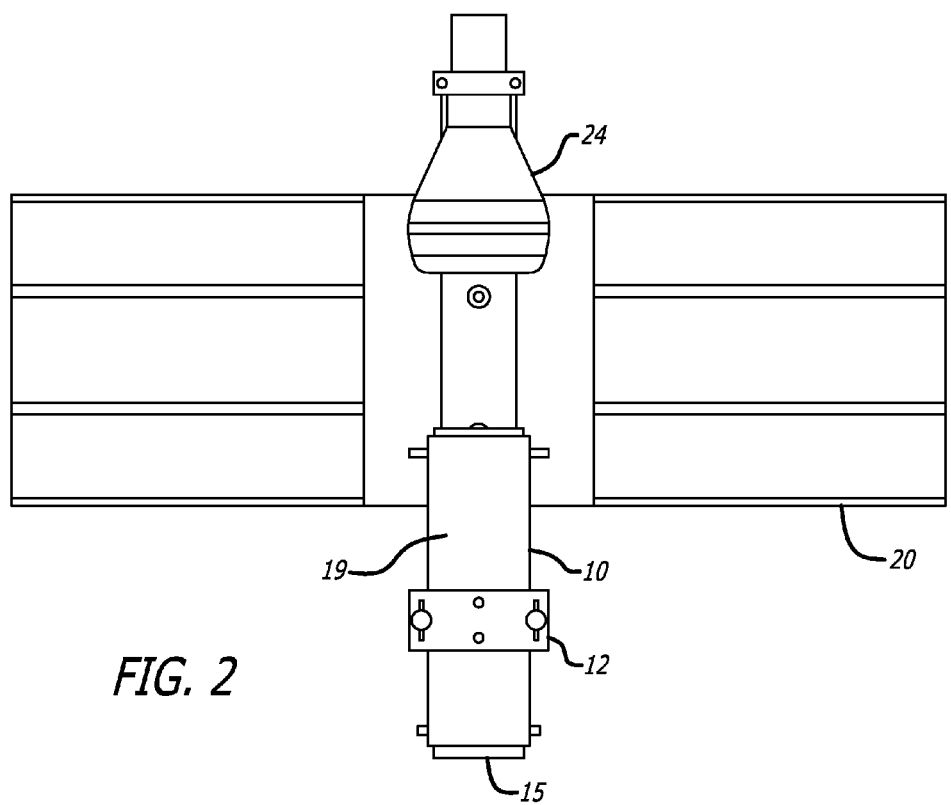
FIG. 2 depicts a top view of the embodiment illustrated in FIG. 1 mounted onto a laser diffraction measuring apparatus showing the zone traveled by a powder plume.

FIG. 2 depicts a schematic representation of a top view of a device embodiment mounted onto a holder and depicting how the device can be attached to a laser diffraction measuring apparatus, for example, device 20. As seen in FIG. 2, device 10 can be adapted to replace a standard holder provided with, for example, apparatus 20, which is mounted onto a mounting means or plate through, for example, a bracket 12 which is moveable and allows a plume to be measured at various distances from a laser beam. Device 10 can comprise a clamp, for example, bracket 12 which holds device 10 in a horizontal plane parallel with a low vacuum, bell-shaped entry port 24, which can be provided with an apparatus. In this manner, a powder plume emitted from an inhaler in the device can be evacuated into the vacuum system immediately after it is read without causing powder to linger in the ambient air after measurements are made. Measurements on this set up with a laser diffraction apparatus can be obtained for a plume as soon as a plume is emitted from an inhaler to the point it enters the vacuum 24. In one embodiment, a powder plume can be measured for a length of predetermined length of time depending on the inhaler type. For example, high resistance inhalers described herein in conjunction with U.S. Pat. Nos. 7,305,986, 7,464,706 and U.S. patent application Ser. No.

12/484,129 (2009/0308391) can generated a powder plume in less than 10 seconds. In embodiments herewith, measurements can be set at predetermined times such as for 10 seconds or less from the start of a plume discharge from an inhaler. In some embodiments, measurements can be made with the present system for shorter or longer durations depending on the inhaler internal air conduits or pathways.

Figure 3:
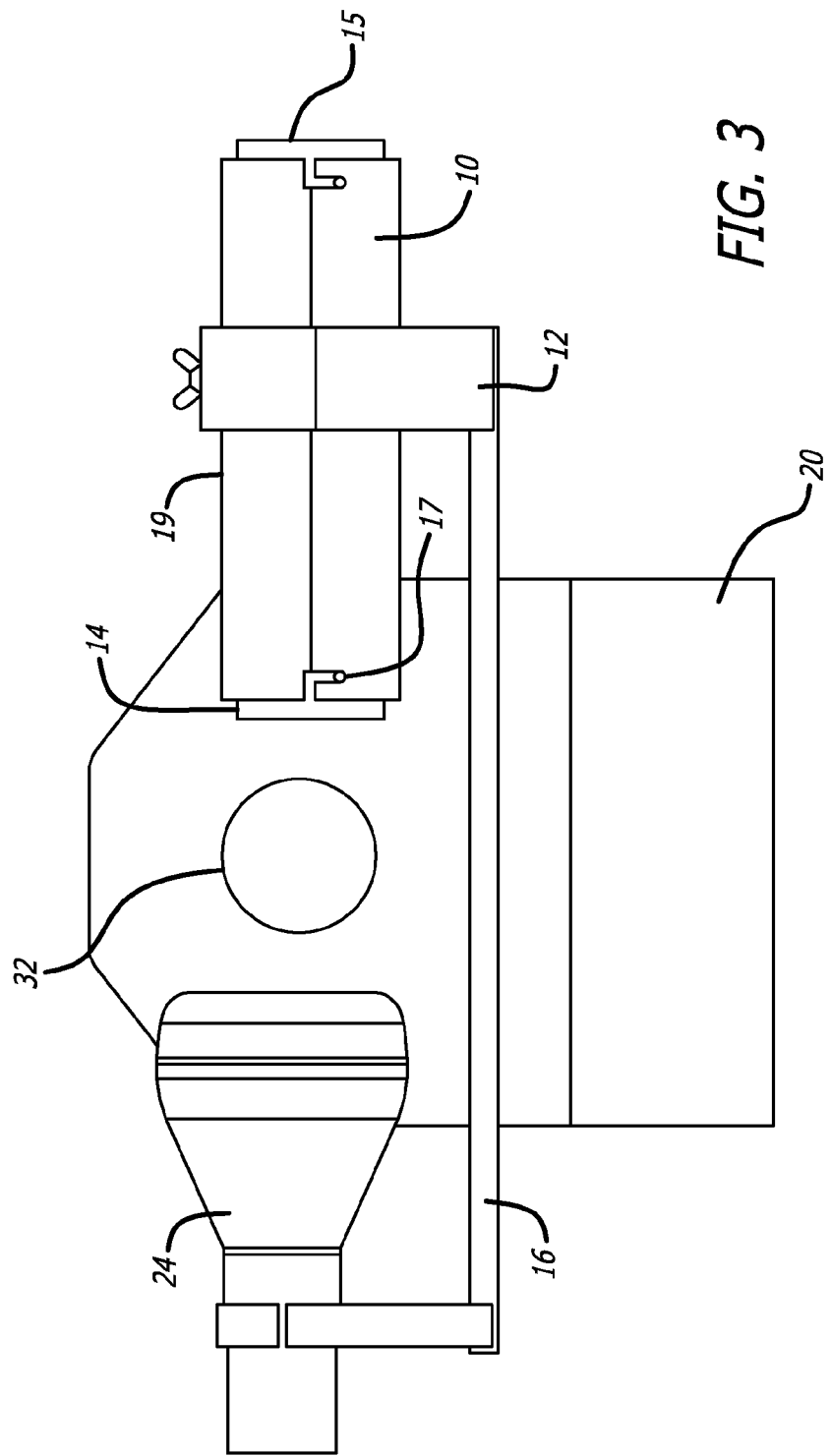
FIG. 3 depicts a schematic representation of a cut away, side view of the embodiment illustrated in FIG. 1 showing the device positioned onto a laser diffraction apparatus.

FIG. 3 depicts a schematic representation of a cut away, side view of one embodiment, showing the device 10 positioned onto a laser diffraction set up being held by bracket 12 comprising a clamp as securing means, wherein device 10 comprises two end caps 14, 15 securely adapted to cylinder 19 by pins 26, 27 and slots 17 and showing the relative distance of the proximal end 11 and the laser beam area 32 and vacuum hose 24 mounted in the same parallel plane and facing proximal end 11. FIG. 3 also shows that device 10 can also be mounted on a track, such as track 16, to be attached to the laser diffraction analytical system.

Figure 4:
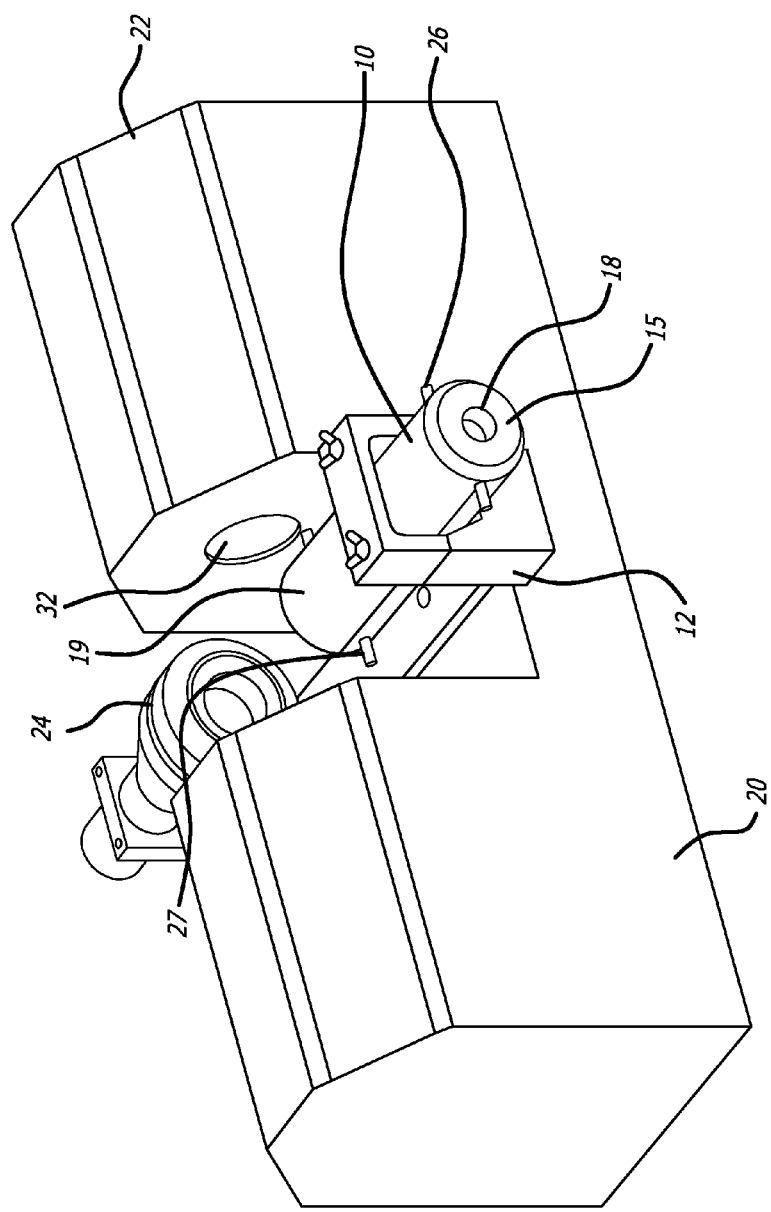
FIG. 4 depicts a perspective view of a schematic drawing of a device mounted onto a laser diffraction apparatus for use.

FIG. 4 depicts a schematic representation in a perspective view of how the exemplified device embodiment can be mounted onto a laser diffraction apparatus 20 for use. In this embodiment, the present device 10 is adapted with bracket 12 as a replacement part for the standard chamber part, for example, the Inhaler Dispersing Unit (Sympatec GmbH), provided with the unit 20, 22. FIG. 4 shows device 10 comprising a cylindrical structure having end cap 14 configured with an opening 18 to receive a hose or tube which is connected to a flow meter to allow pressurized air or gas to enter chamber 19.

FIG. 5 depicts a schematic illustration of an embodiment of the device in cross-section through its mid-longitudinal axis showing an inhaler adapted to the holder in an in-use position. In certain embodiments, for example, in FIG. 5, the device can further comprise O-rings 23, 25 configured with the end caps 14, 15 to further ensure a tight seal under positive pressure can be attained so that flow travels only through the inhaler with a powder dose as if the inhaler 30 would be in use by a subject. In the embodiment illustrated in FIGS. 1-5, adaptor 10 is attached to a system by mounting means 12 which is attached to a base plate. In this embodiment, the chamber can be removed for cleaning if needed, but can remain attached at all times, however, the proximal end components can be removed to install a new inhaler or load the inhaler with a new dose or cartridge containing powder after each use.

Figure 6:
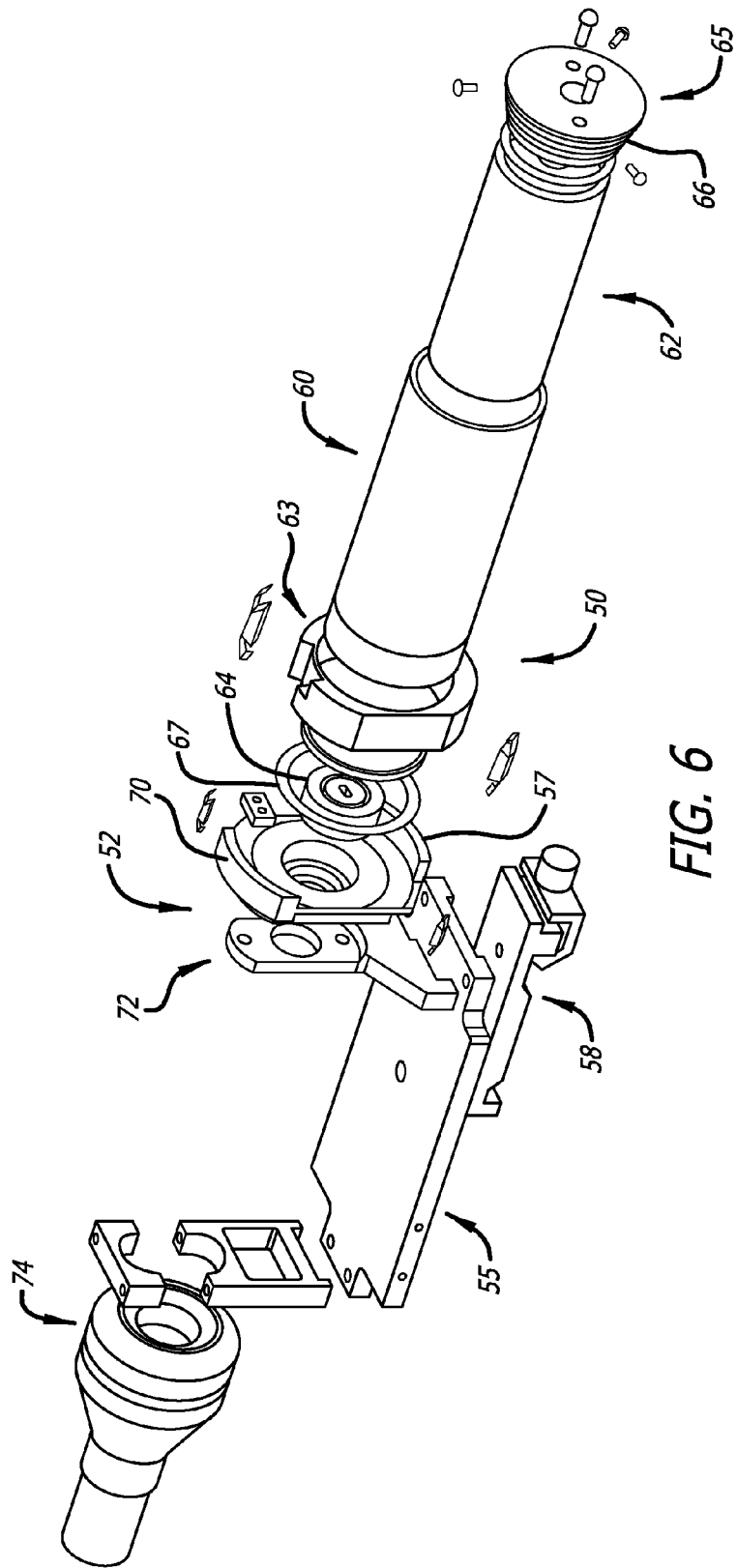
FIG. 6 depicts a perspective view of an alternate embodiment of the device for adapting to a laser diffraction particle measuring apparatus in a partially exploded configuration.

FIGS. 6-9 depict another embodiment of an adaptor device for use with a laser diffraction apparatus for measuring particle size distribution of a powder plume emitted from a dry powder inhaler. In this embodiment, the proximal end of device 50 is attachable to a mounting means and can remain permanently attached to a base plate 55 through the mounting plate 72 after each use. In this embodiment, the removable component of the device 50 is chamber 60 which comprises a mechanism configured to be clamped into an end cap 57 of the device 60. FIG. 6 illustrates an exploded view of the adaptor device 50 showing all component parts. As shown in FIG. 6, adaptor 50 has a cylindrical structure, comprising a chamber 60 having a collar 63 which is fixed and engageable to a proximal end cap or mouthpiece mounting case 70 and a distal end cap 65 having a hole for connecting a hose to allow the source of positive pressure into the interior of the chamber and including a spacer 62 and a bracket 63 attachable to an inhaler mounting means such as mouthpiece adaptor 64 and mouthpiece mounting case 70 which is configured to be adaptable to a side or mounting plate 72 connected to a base plate 55 proximal to a source of a laser beam. In this and other embodiments, the device 50 can comprise one or more gaskets, such as gasket 67 and one or more o-rings 66 which help for tight seals with the end caps and/or clamps. Mouthpiece adaptor 64 can be configured to have a design to fit a corresponding inhaler mouthpiece as long as a seal can be formed. In certain embodiments, mouthpiece adaptor 64 can be made of, for example, a rubber or plastic material that is not porous to a gas. Mouthpiece mounting case 70 and mounting plate 72 each have a central opening to allow a mouthpiece of an inhaler to protrude through the opening so that a powder plume exiting the inhaler is not disturb or affected during transit. Base plate 55 can comprise a clamp for adapting to the laser diffraction system and is configured to be movable to adjust the distance that a powder plume would traverse while being measured. In embodiments herewith, a vacuum hose 74 can also be provided with the adaptor 50. In this embodiment, an inhaler body is enclosed within chamber 60 in use. In some embodiments, spacer 62 can be insertable into the interior of the chamber and is configured with different wall thickness and various lumen diameters and in various material depending on the inhaler size in order to maintain the space within the chamber 60 constant surrounding an inhaler in use with the same inhaler type or when using different inhalers.

Figure 7:
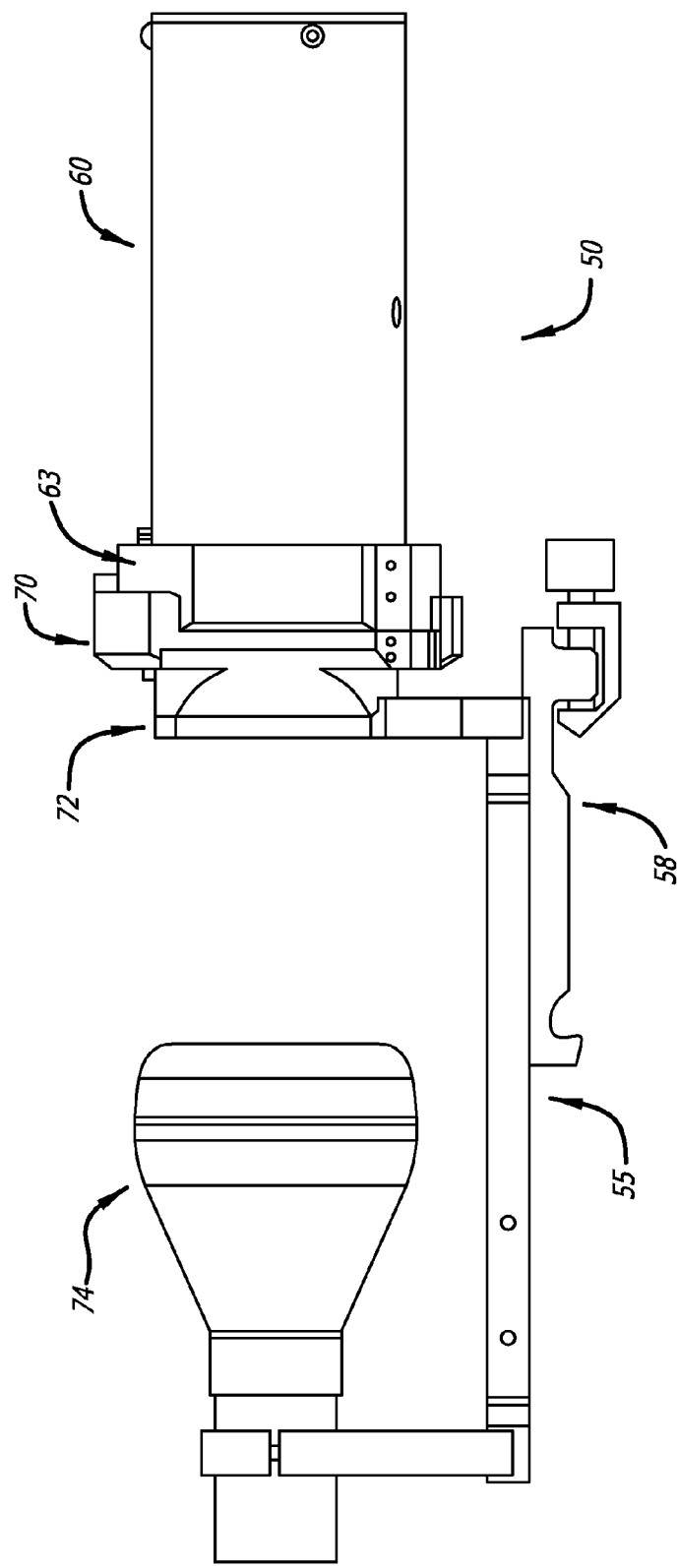
FIG. 7 depicts a side view of the embodiment illustrated in FIG. 6 attached to a mounting mechanism on the mounting plate.
Figure 8:
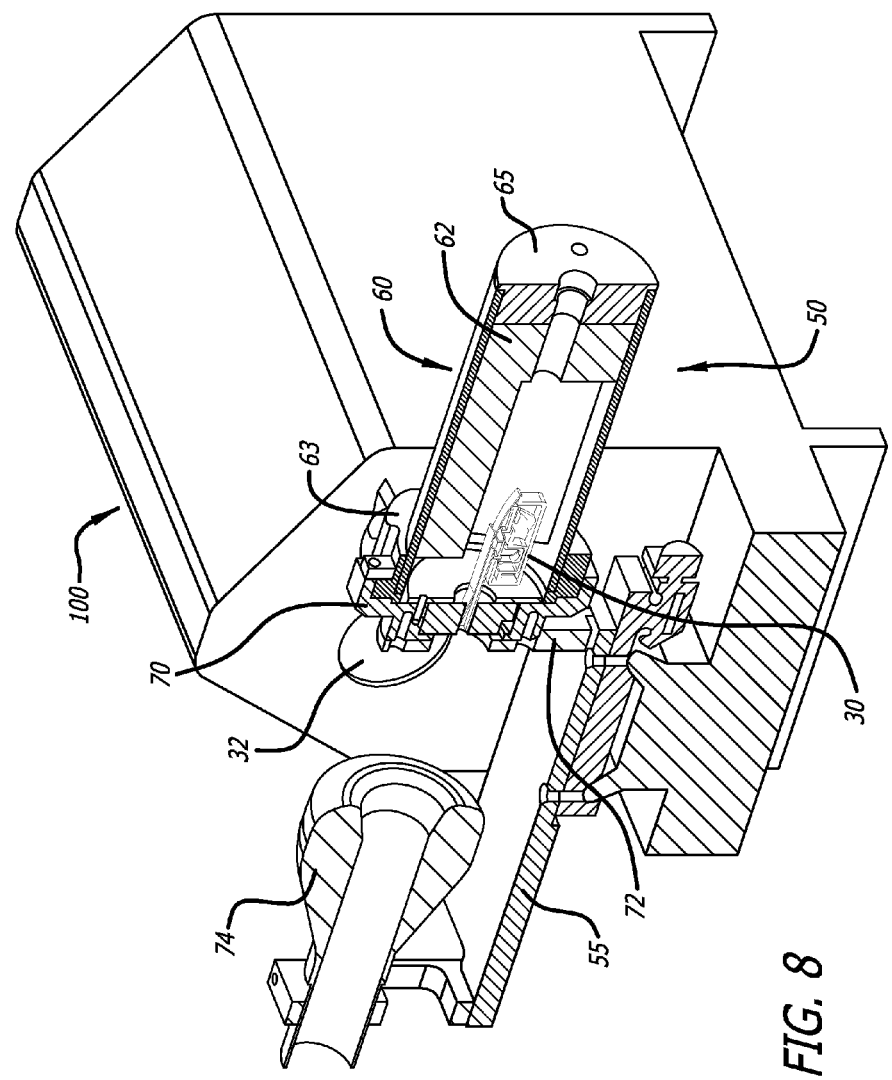
FIG. 8 depicts an perspective view of the adaptor of FIG. 6 in cross section through its longitudinal axis with an inhaler mounted in place.

FIG. 7 is a schematic diagram of a side view of an assembled device 50 adapted for use showing chamber 60, end cap or mouthpiece adaptor case 70 connected to the mounting plate 72, which is attached to base plate 55. FIG. 8 illustrates a cross section through the longitudinal axis of the adaptor device 50 with an inhaler 30 installed for testing, mounted in a laser diffraction apparatus 100, and comprising a chamber 60, a spacer 62; an end cap 65 and attached by the end cap 70 to collar 63 and ready for use. FIG. 8 also illustrates the inhaler mouthpiece adapted to the mouthpiece holder and its proximity to the source of the laser beam at lens 32.

Figure 9:
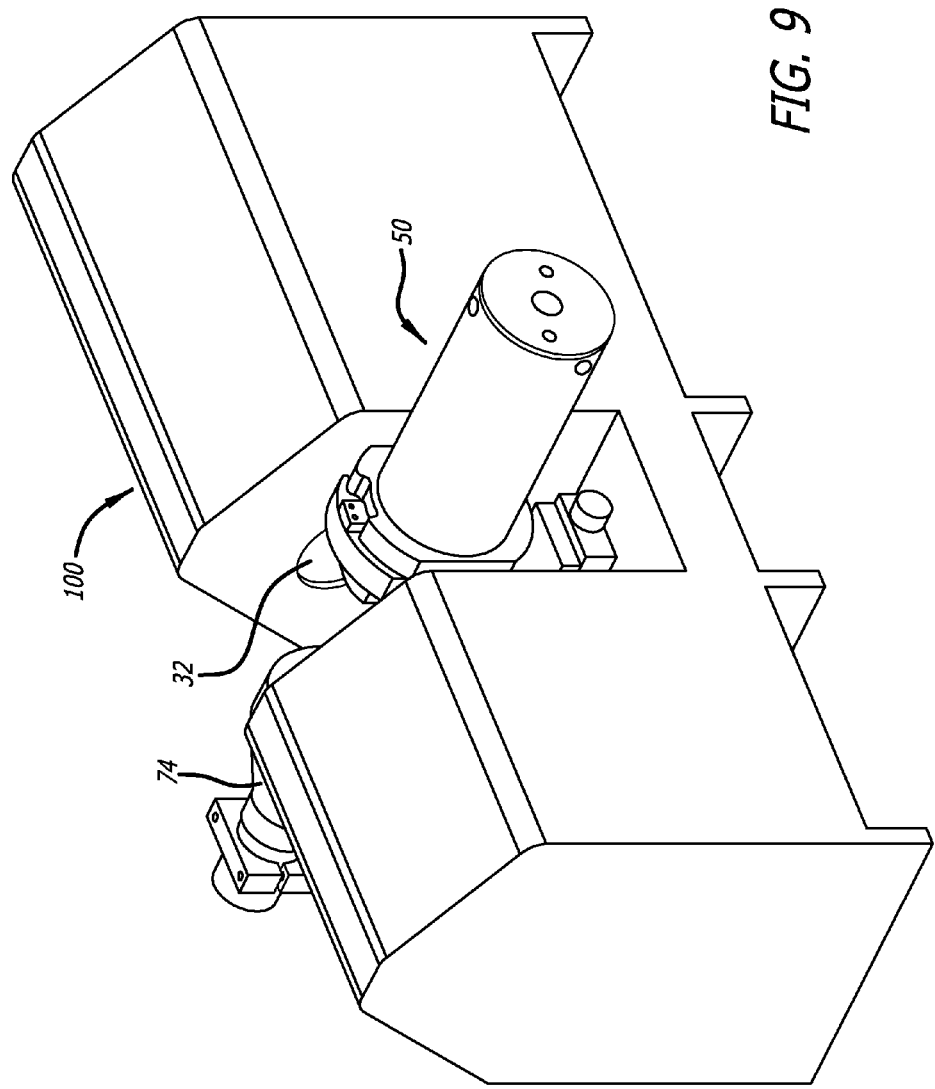
FIG. 9 depicts the embodiment illustrated in FIGS. 6-9 attached to a mounting mechanism on a laser diffraction apparatus.

FIG. 9 illustrates a perspective view of a laser diffraction apparatus 100 with adaptor 50 assembly connected thereto and in position for use, but without being connected to a source of positive pressure.

In another embodiment, predetermined pressure profiles applied can be of simulations of actual patient inspiratory profiles. The profiles are generated by an automated piston—cylinder assembly, such as the one disclosed in U.S. Provisional Patent Application Ser. No. 61/257,813, entitled "Apparatus and Method for Simulating Inhalation Efforts." In one embodiment, the piston motion is driven by a motor controlled linear slide. The cylinder is directly connected to the chamber containing the inhaler. The cylinder motion can generate profile simulations with high accuracy and can compensate for variations in inhaler resistance.

In one embodiment and during operation using the present device, as the simulated flow profile is applied to the inhaler, the plume is discharged through the inhaler in a way that is similar to which it would be characteristic during patient therapy. The powder plume travels through the chamberless and/or ambient laser measurement zone towards the vacuum cone. Once past it, the powder is collected via a vacuum pulled through a cone ensuring that it does not contaminate any of the test environments. Because the plume does not have to travel through a chamber, for example, a cross shaped chamber used with standard methods, which contains various vent ports, its trajectory and turbulence are controlled by the aerodynamic properties and momentum of its individual particles. This has 2 advantages: first, the equipment deposition is minimized and deposition of powder particles on the lens is eliminated; a user no longer needs to repeatedly and tediously clean the system between groups of inhalations, and second, the dispersion of the plume can be controlled by the applied inspiratory flow profile. In the embodiments exemplified herewith, outside influences, including turbulence zones, and vent streams are minimized allowing a user to accurately quantify plume properties.

In one embodiment of the present configuration, data from the laser diffraction measurements can be collected by the system in a time interval equal to that of a plume moving past it the laser measuring zone. In this embodiment, a user can therefore ensure more accurate and repeatable evaluation of a powder plume emitted from the dry powder inhaler by minimizing repeated counting of particles recirculating in the laser measurement area when measuring the plume inside a chamber. The present device and method therefore minimize variations in particle distribution measurements taken form a powder plume emitted from an inhaler. Different flow profiles can create plumes with different characteristics which can be analyzed by the system as they move past the laser measurement area. The measurement can be correlated to any achievable inspiratory or inhalation profile.

In the embodiments described herein, the device 10 can enable measurement of inspiratory flow profiles through a programmable flow control valve attached between the gas source of positive pressure and the inhaler chamber. In one embodiment, the device 10 can be adapted by connecting programmable piston-cylinder assembly to the chamber 19 containing an inhaler with a dry powder in a cartridge. The present embodiment can also eliminate contamination of the lenses used with the laser diffraction apparatus and system by the powder plume discharge from an inhaler during use and thus reducing error in particle counting associated during a test. The present method reduces flow turbulence which may cause multiple counting of the same particles trapped in the flow turbulent chamber of previous systems and eliminates repeated cleaning after use. The present method also negates common venting and timing challenges associated with common industry systems, which operate with vacuum fixtures only and the like.

In certain embodiments, the device 10 can allow for control of the expansion of the plume exiting an inhaler by adjusting vacuum pressure, inhaler chamber pressure and the distance between the inhaler chamber and the vacuum source. In one embodiment, the device 10 allows for controlling measurement trigger conditions which can be used to correlate particle size distribution to measured mass for an experiment. In this embodiment, the correlation can be used to estimate amount of powder measured for the measurement at the experimental conditions. In the embodiments described herein, the device and method provide a user with the advantage of controlling the size and time of the plume when compared to traditional fixed chambers using vacuums as a means for creating the plume.

Dry powder inhalers such as those described in U.S. Pat. Nos. 7,305,986, 7,464,706 and U.S. patent application Ser. No. 12/484,129 (2009/0308391), have been tested using the device described herein.

EXAMPLE

Measurements of the particle size distribution with a device embodiment adapted to a laser diffraction apparatus (Helos Laser Diffraction Sensors, Sympatec GmbH) were made of a formulation of various amounts in milligrams (mgs) of an insulin and fumaryl diketopiperazine particles provided in a cartridge mounted onto an inhaler system such as those described in U.S. Pat. Nos. 7,305,986, 7,464,706 and U.S. patent application Ser. No. 12/484,129 (2009/0308391). The adaptor device is mounted onto the Helos apparatus. The device is attached at one end to a tubing, which is adapted to a flow meter (TSI, Inc. Model 4043) and a valve to regulate pressure or flow from a compressed air source. An inhaler as shown in FIG. 5 is adapted to the device and the inhaler also contains a cartridge containing the dry powder formulation. Once activated and the laser beam is ready to measure a plume, a pneumatic valve is actuated to allow the powder to be discharged from the inhaler. The laser system measures the plume exiting the inhaler device automatically based on predetermined measurement conditions. The laser diffraction system is operated by software integrated with the apparatus and controlled by computer program. Measurements were made of samples containing different amounts of powder and different powders. The measurement conditions are as follows:

Flow rate settings during measurements are set at peak flows of 10 to 40 L/min;

Laser measurement start trigger conditions: when >0.6% laser intensity is detected on a particular detector channel;

Laser measurement end trigger conditions: when <0.4% laser intensity is detected on a particular detector channel;

Vacuum source is set at 250 millibars or at flow rates greater than 30 L/min.

Distance between vacuum source and inhaler chamber is approximately 9.525 cm.

Figure 10:
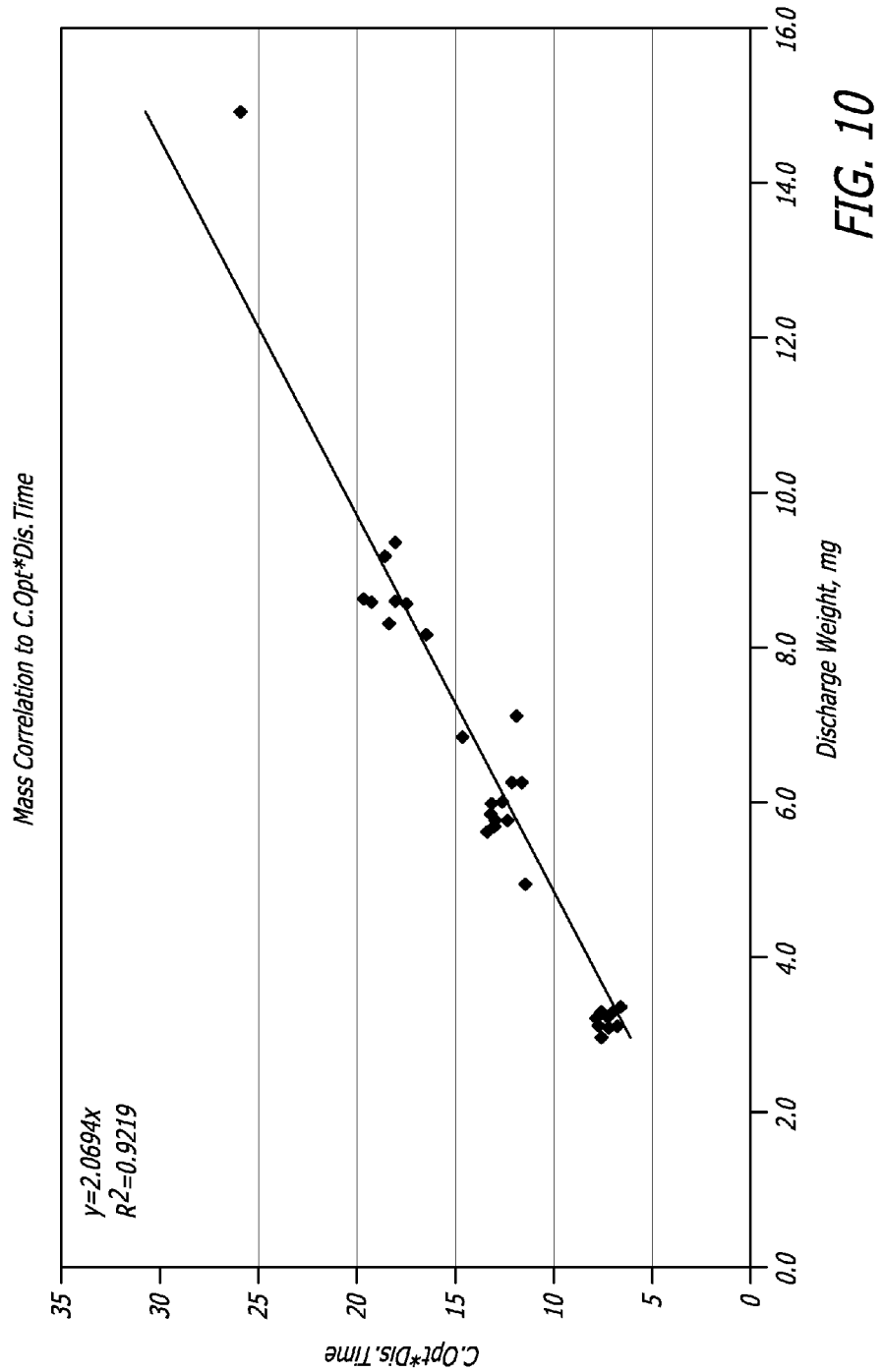
FIG. 10 depicts a graph of the optical concentration times the measurement time versus actual discharged mass which were made with laser diffraction apparatus equipped with a device embodiment described herewith adapted with a dry powder inhaler and a dry powder composition for inhalation comprising insulin and fumaryl diketopiperazine particles.

Measurements obtained from the laser diffraction apparatus can be correlated to mass of powder discharged during the measurement. Once the correlation is established it can be used to estimate the amount of powder measured during the measurement at the experimental conditions for that particular measurement. Cartridge weights were determined before and after powder discharge from the inhaler to determine discharged powder weights. Once the powder plume is measured, the data is analyzed and graphed. Optical concentration and measurement duration were obtained. FIG. 10 depicts data obtained with the claimed device as described above for multiple samples containing different amounts of powder tested. The data are plotted as a linear regression curve to show the correlation between amounts of powder (x-axis) and the optical concentration multiplied by measurement time (y-axis) to show the amount of powder measured by the laser diffraction system which correlates to the amount of powder emitted by the inhaler used.

Figure 11:
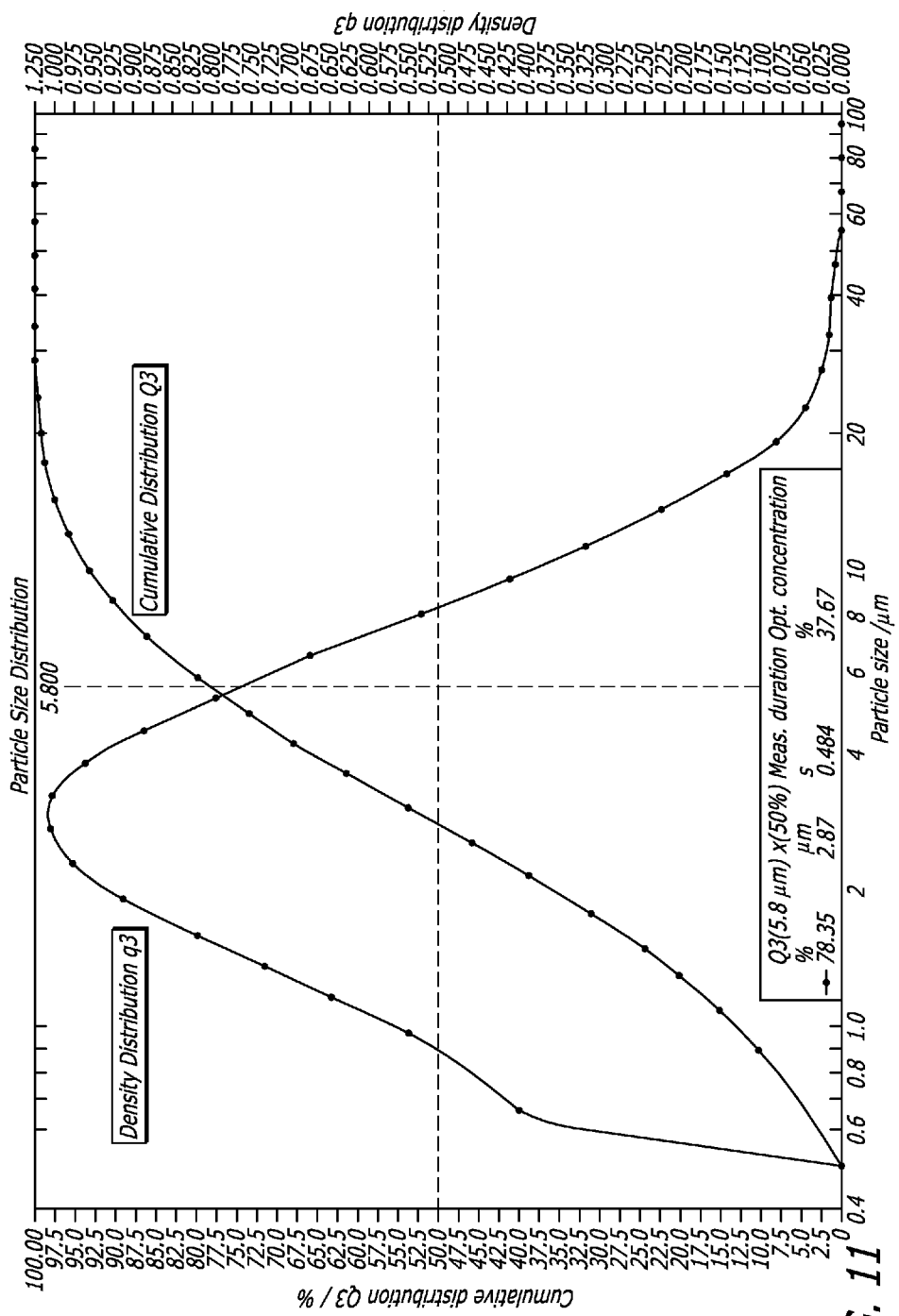
FIG. 11 depicts data obtained from the experiment described in FIG. 10, showing the particle size distribution obtained with a laser diffraction apparatus adapted with an embodiment of the device described herein and an inhaler containing a dry powder formulation for inhalation comprising insulin and fumaryl diketopiperizine particles.

FIG. 11 illustrates data of the particle size distribution of a 10 mg sample containing particles of a formulation comprising insulin and a diketopiperazine measured by laser diffraction system with the claimed device using the conditions described above. FIG. 11 indicates that the laser system using the claimed device resulted in 78.35% of the measured particles having a particle size of <5.8 μm. The laser detected 37.67% optical concentration during the measurement duration of 0.484 seconds at the above measurement conditions.

The preceding disclosures are illustrative embodiments. It should be appreciated by those of skill in the art that the devices, techniques and methods disclosed herein elucidate representative embodiments that function well in the practice of the present disclosure. However, those of skill in the art should, in light of the present disclosure, appreciate that many changes can be made in the specific embodiments that are disclosed and still obtain a like or similar result without departing from the spirit and scope of the invention.

Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the following specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques. Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements.

The terms "a" and "an" and "the" and similar referents used in the context of describing the invention (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g. "such as") provided herein is intended merely to better illuminate the invention and does not pose a limitation on the scope of the invention otherwise claimed. No language in the specification should be construed as indicating any non-claimed element essential to the practice of the invention.

The use of the term "or" in the claims is used to mean "and/or" unless explicitly indicated to refer to alternatives only or the alternatives are mutually exclusive, although the disclosure supports a definition that refers to only alternatives and "and/or."

Groupings of alternative elements or embodiments of the invention disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is herein deemed to contain the group as modified thus fulfilling the written description of all Markush groups used in the appended claims.

Preferred embodiments of this invention are described herein, including the best mode known to the inventors for carrying out the invention. Of course, variations on those preferred embodiments will become apparent to those of ordinary skill in the art upon reading the foregoing description. The inventor expects those of ordinary skill in the art to employ such variations as appropriate, and the inventors intend for the invention to be practiced otherwise than specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Specific embodiments disclosed herein may be further limited in the claims using consisting of or consisting essentially of language. When used in the claims, whether as filed or added per amendment, the transition term "consisting of" excludes any element, step, or ingredient not specified in the claims. The transition term "consisting essentially of" limits the scope of a claim to the specified materials or steps and those that do not materially affect the basic and novel characteristic(s). Embodiments of the invention so claimed are inherently or expressly described and enabled herein.

Furthermore, numerous references have been made to patents and printed publications throughout this specification. Each of the above cited references and printed publications are herein individually incorporated by reference in their entirety.

Further, it is to be understood that the embodiments of the invention disclosed herein are illustrative of the principles of the present invention. Other modifications that may be employed are within the scope of the invention. Thus, by way of example, but not of limitation, alternative configurations of the present invention may be utilized in accordance with the teachings herein. Accordingly, the present invention is not limited to that precisely as shown and described.

We claim:

1. A method of measuring at least one particle characteristic with a laser diffraction apparatus, comprising:
- providing a device comprising a chamber and configured to hold a breath-powered, dry powder inhaler in a closed environment; said breath-powered inhaler having a body and comprising a dry powder formulation;
- installing said breath-powered inhaler into said chamber so that the body of said dry powder inhaler is enclosed within said chamber;
- providing positive pressure into said chamber of said device to create a flow of air or gas through said dry powder inhaler to discharge particles of said dry powder formulation, and
- measuring said at least one particle characteristic with the laser diffraction apparatus,
- wherein the particles are emitted from the inhaler into a chamberless and/or ambient environment.

2. The method of claim 1, wherein said at least one particle characteristic is particle density.

3. The method of claim 1, wherein said at least one particle characteristic is particle size distribution.

4. The method of claim 1, wherein the breath-powered, dry powder inhaler comprises a mouthpiece.

5. The method of claim 4, wherein said mouthpiece forms an air pathway from the chamber to the chamberless and/or ambient environment.

6. The method of claim 1, wherein the step of providing positive pressure into said chamber is attained by a source of pressurized gas from a flow controller system comprising a valve or a syringe pump.

7. The method of claim 1, wherein the positive pressure applied is greater than 1 kPa.

8. The method of claim 1, wherein the step of measuring with a laser diffraction apparatus occurs concurrent with emission of particles from the dry powder inhaler.

9. A method of measuring at least one particle characteristic with a laser diffraction apparatus, comprising:
- providing positive pressure into a chamber configured to hold an inhaler in a closed environment to create a flow of air or gas through said inhaler to emit particles of a formulation housed within the inhaler into a chamberless and/or ambient environment, and
- measuring said at least one particle characteristic with the laser diffraction apparatus.

10. The method of claim 9, wherein said at least one particle characteristic is particle density.

11. The method of claim 9, wherein said at least one particle characteristic is particle size distribution.

12. The method of claim 9, wherein the inhaler comprises a mouthpiece.

13. The method of claim 12, wherein said mouthpiece forms an air pathway from the chamber to the chamberless and/or ambient environment.

14. The method of claim 9, wherein the step of providing positive pressure into said chamber is attained by a source of pressurized gas from a flow controller system comprising a valve or a syringe pump.

15. The method of claim 9, wherein the positive pressure applied is greater than 1 kPa.

16. The method of claim 9, wherein the step of measuring with a laser diffraction apparatus occurs concurrent with emission of particles from the dry powder inhaler.

17. The method of claim 9, wherein the inhaler is a breath powered, dry powder inhaler.

18. The method of claim 9, wherein the formulation is a dry powder.

19. A method of measuring at least one particle characteristic with a laser diffraction apparatus, comprising:
providing positive pressure into a chamber configured to hold a breath powered, dry powder inhaler including a mouthpiece in a closed environment to create a flow of air or gas through said breath powered, dry powder inhaler to emit particles of a dry powder formulation housed within the breath powered, dry powder inhaler into a chamberless and/or ambient environment, and
measuring said at least one particle characteristic with the laser diffraction apparatus when particles are emitted from the breath powered, dry powder inhaler,
wherein said mouthpiece forms an air pathway from the chamber to the chamberless and/or ambient environment.

* * * * *